United States Patent [19]

Yokoe et al.

[11] Patent Number: 4,947,855
[45] Date of Patent: Aug. 14, 1990

[54] BLOOD PRESSURE MEASURING APPARATUS

[75] Inventors: Hifumi Yokoe, Kosai; Chikao Harada, Nagoya, both of Japan

[73] Assignee: Colin Electronics Co., Ltd., Japan

[21] Appl. No.: 310,898

[22] Filed: Feb. 16, 1989

[51] Int. Cl.⁵ .............................................. A61B 5/021
[52] U.S. Cl. .................................. 128/672; 128/687; 128/690
[58] Field of Search ................. 128/672, 677, 687–690

[56] References Cited

U.S. PATENT DOCUMENTS

| | | | |
|---|---|---|---|
| 3,219,035 | 11/1965 | Pressman et al. | 128/672 |
| 4,185,621 | 1/1980 | Morrow | 128/672 |
| 4,423,738 | 1/1984 | Newgard | 128/672 |
| 4,799,491 | 1/1989 | Eckerle | 128/672 |
| 4,802,488 | 2/1989 | Eckerle | 128/672 |
| 4,830,017 | 5/1989 | Perry et al. | 128/677 X |

FOREIGN PATENT DOCUMENTS 0289700 11/1988 European Pat. Off. .
293424 11/1988 Japan .
2118719 11/1983 United Kingdom .
2191587 12/1987 United Kingdom .

Primary Examiner—Kyle L. Howell
Attorney, Agent, or Firm—Oliff & Berridge

[57] ABSTRACT

A blood pressure measuring apparatus having a housing detachably set on a body surface of a subject, a pressure sensor accommodated in the housing such that the pressure sensor is opposed to the body surface when the housing is set on the body surface, the pressure sensor being pressed against the body surface so as to detect pulse wave produced from an arterial vessel of the subject, the pressure sensor generating pulse wave signal representing the detected pulse wave, a pressing device for pressing the pressure sensor against the body surface, and a control device for determining blood pressure in the arterial vessel based on the pulse wave signal supplied from the pressure sensor, the pressing means and the control means being accommodated in the housing.

5 Claims, 3 Drawing Sheets

BLOOD PRESSURE MEASURING APPARATUS

BACKGROUND OF THE INVENTION

1. Field of the Invention

The present invention relates to a blood pressure measuring apparatus and particularly to improvements in such an apparatus which measures blood pressure based on pulse wave produced from a blood vessel of a living body.

2. Related Art Statement

Pulse wave is generally defined as pressure wave, or oscillation of the wall of a blood vessel, produced with heart beat of a living body and transmitted through the blood vessel. There has been proposed a device for determining blood pressure based on the pulse wave. The Inventors and others filed Japanese Pat. Application No. 62-130879 on May 27, 1987 in which they disclosed a pulse wave detecting device which is capable of determining maximum and minimum blood pressure based on the detected pulse wave. The device has (a) a housing detachably set on a body surface of a subject, (b) a pressure sensor accommodated in the housing such that the pressure sensor is opposed to the body surface when the housing is set on the body surface, the pressure sensor being pressed against the body surface so as to detect pulse wave produced from an arterial vessel of the subject, the pressure sensor generating pulse wave signal representing the detected pulse wave, (c) pressing means for pressing the pressure sensor against the body surface, and (d) a control circuit for determining blood pressure in the arterial vessel based on the pulse wave signal supplied from the pressure sensor. This device permits easier blood pressure measurement than a prior device using an inflatable cuff which occludes blood flow for blood pressure measurement as a result of compressing an upper arm of a subject. The above-indicated Japanese Pat. Application was laid open under Publication No. 63-293424 on Nov. 30, 1988.

However, the above-indicated pulse wave detecting device is not easy to handle or handy to carry because the pressing means and the control circuit are disposed apart from the housing and connected thereto via air piping and electric wiring, respectively. Furthermore, such air piping and/or electric wiring restricts activity of the subject to some extent.

SUMMARY OF THE INVENTION

It is therefore an object of the present invention to provide a blood pressure measuring apparatus permitting easy use and carrying-about, and free activity of a subject.

The above object has been achieved by the present invention, which provides a blood pressure measuring apparatus having (a) a housing detachably set on a body surface of a subject, (b) a pressure sensor accommodated in the housing such that the pressure sensor is opposed to the body surface when the housing is set on the body surface, the pressure sensor being pressed against the body surface so as to detect pulse wave produced from an arterial vessel of the subject, the pressure sensor generating pulse wave signal representing the detected pulse wave, (c) pressing means for pressing the pressure sensor against the body surface, and (d) control means for determining blood pressure in the arterial vessel based on the pulse wave signal supplied from the pressure sensor, the apparatus comprising the improvements that the pressing means and the control means are accommodated in the housing.

In the blood pressure measuring apparatus constructed as described above, all of the pressure sensor, pressing means and control means are accommodated in the housing. Accordingly, blood pressure measurement is easily performed by setting the housing (apparatus) on a body surface of a subject and attaching it thereto. Also, the present apparatus permits easier use and conveyance thereof than the conventional apparatus of the type having a housing and air piping and electric wiring connecting between the housing and other external elements. Therefore, the present apparatus is free from the conventionally encountered problem that the activity of the subject is limited by the air piping and/or electric wiring.

According to a preferred embodiment of the present invention, the blood pressure measuring apparatus further comprises a display device for displaying the blood pressure, the display device being provided on one of opposite outer surfaces of the housing, the other of the opposite outer surfaces being opposed to the body surface while the housing is set on the body surface. Thus, the display device is externally visible or observable.

In another embodiment of the apparatus of the invention, the pressing means includes an externally threaded member secured to the housing and having an axis, the axis being substantially perpendicular to the body surface when the housing is set on the body surface, an internally threaded member engaged with the externally threaded member, and having a multiplicity of outer teeth formed along an outer circumference thereof, a motor having an output shaft, and a pinion engaged with the outer teeth of the internally threaded member and secured to the output shaft of the motor. Upon operation of the motor the internally threaded member is moved toward, and retracted away from, the body surface while being rotated around the externally threaded member as a result of rotation of the pinion driven by the motor.

In a modified form of the above embodiment, the pressure sensor includes a semiconductor chip, a plurality of pressure-sensitive semiconductor elements arranged along a line on the semiconductor chip, each of the semiconductor elements generating the pulse wave signal, and a cylindrical member co-axial with the externally and internally threaded members, the cylindrical member being fitted at one of axial ends thereof on the externally threaded member such that the cylindrical member is not rotatable relative to the externally threaded member and is movable relative to the externally threaded member along the co-axis, the cylindrical member being engaged at the one axial end thereof with the internally threaded member such that the cylindrical member is rotatable relative to the internally threaded member about the co-axis and is not movable relative to the internally threaded member along the co-axis, the semiconductor chip being secured to the other axial end of the cylindrical member. Upon the operation of the motor, the semiconductor chip is moved toward the body surface together with the cylindrical member. In this case, the control means may be adapted to select one of the plurality of pressure-sensitive semiconductor elements which is located right above the arterial vessel, the control means monitoring the blood pressure of the subject based on the pulse wave signal from the selected semiconductor element.

In another modified form of the above-indicated embodiment, the control means controls pressing force of the pressing means applied to the pressure sensor, by changing operation amount of the motor based on the pulse wave signal from the pressure sensor.

BRIEF DESCRIPTION OF THE DRAWINGS

The above and optional objects, features and advantages of the present invention will be better understood by reading the following detailed description of the presently preferred embodiment of the invention, when considered in connection with the accompanying drawings, in which.

DETAILED DESCRIPTION OF THE PREFERRED EMBODIMENT

Figure 1:
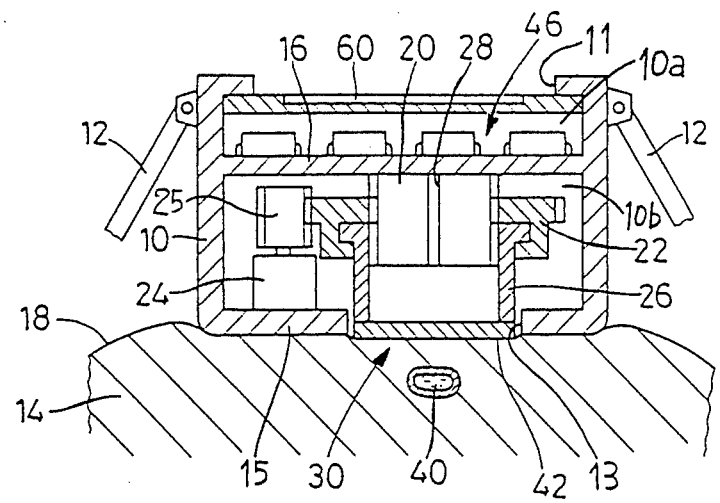
FIG. 1 is a cross-sectional view of a preferred embodiment of the blood pressure measuring apparatus of the present invention.

Referring first to FIG. 1, there is shown a blood pressure measuring apparatus of the present invention. In the figure, reference numeral 10 designates a housing which is detachably set on a surface 18 of a wrist 14 of a subject with the help of a band 12. The housing 10 is separated into an upper and a lower room 10a, 10b by an intermediate partition wall 16. In the lower room 10b that is opposed to the wrist surface 18 when the apparatus (housing 10) is set on the surface 18, an externally threaded member 20 is secured to the intermediate partition wall 16 such that an axis of the externally threaded member 20 is substantially perpendicular to the wrist surface 18 when the housing 10 is set on the surface 18. An internally threaded nut member 22 is threadedly engaged with the externally threaded member 20. The nut member 22 has a multiplicity of teeth along an outer circumference thereof which teeth engage a pinion 25 secured to an output shaft of a motor 24.

A cylindrical presser member 26 is fitted at an upper axial end thereof on a lower axial end of the externally threaded member 20, such that the presser member 26 is not rotatable relative to the externally threaded member 20 and is movable relative to the same 20 vertically as viewed in FIG. 1, namely, along the axis of the member 20. This arrangement is assured by engagement between a groove 28 axially extending in an outer threaded surface of the externally threaded member 20, and a mating ridge (not shown) formed in an inner surface of the presser member 26. Moreover, the presser member 26 is engaged at the upper end thereof with the nut member such that the presser member 26 is rotatable relative to the nut member 22 and is not movable relative to the same 22. Thanks to this arrangement, upon operation of the motor 24, the nut member 22 is moved downward and upward while being rotated around the externally threaded member 20, and the presser member 26 is slid on the externally threaded member 20 substantially perpendicularly to the body surface 18 together with the nut member 22.

Figure 2:
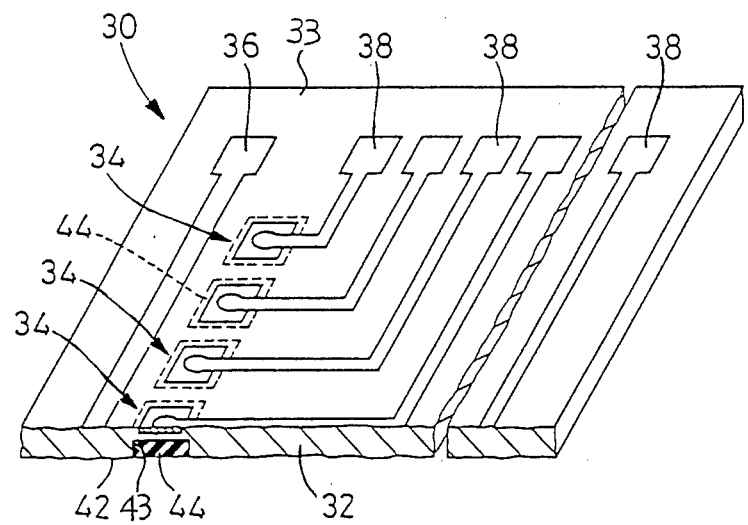
FIG. 2 is a perspective view partially showing a pressure sensor of the apparatus of FIG. 1.

A presser plate 30 is fixed to a lower axial end of the presser member 26 such that, with the housing 10 set on the body surface 18, the presser plate 30 extends perpendicular to the direction in which the presser member 26 is moved, namely, in a direction substantially parallel to the body surface 18. The presser plate 30 is moved through a lower opening 13 formed through a bottom wall 15 of the housing 10 when the motor 24 is operated. As shown in FIG. 2, the presser plate 30 includes a semiconductor chip 32 formed of monocrystalline silicon or the like, and a multiplicity of pressure-sensitive diodes 34 formed on an upper surface 33 of the chip 32. Electrical signals representing pressure variation at interfaces between the chip 32 and the diodes 34 are produced between a common terminal 36 and individual terminals 38 of the diodes 34. With the housing 10 set on the wrist 14, the multiplicity of pressure-sensitive diodes 34 are in row along a line substantially perpendicular to a radial artery 40 (FIG. 1), such that the diodes 34 are equally spaced apart from each other by a suitable distance. The width of each diode 34 as measured in the direction perpendicular to the artery 40 and the equal distance between each pair of adjacent two diodes 34, are pre-determined such that at least three diodes 34 can be located within a body-surface portion right above the artery 40 which portion has a length equal to the diameter or width of the artery 40. The shape or configuration of each diode 34, and the dimension (length) of the same 34 as measured in a direction parallel to the artery 40 are appropriately pre-determined.

At locations on a lower surface 42 of the semiconductor chip 30 which locations are opposite to the locations on the upper surface 33 of the chip 30 where a number of pressure-sensitive diodes 34 are provided, corresponding number of rubber fillers 44 are provided. The rubber fillers 44 are embedded in recesses 43 such that the fillers 44 do not apply any load to the corresponding diodes 34 and such that outer surfaces of the fillers 44 are aligned with the lower surface 42 of the chip 30, namely, the lower surface 42 has no unevenness. With the presser plate 30 pressed against the body surface 18 as a result of operation of the motor 24, the body surface 18 right above and near the radial artery 40 is flattened under the presser plate 30. Thus, the pressure oscillation or pulse wave produced from the artery 40 is transmitted to the pressure-sensitive diodes 34 via the rubber fillers 44. The semiconductor chip 32 has an extremely small thickness, for example 15 μm, at the locations where the recesses 43 for the rubber fillers 44 are provided. The pressure oscillation transmitted to the rubber fillers 44, causes pressure variation at the interfaces between the pressure-sensitive diodes 34 and the semiconductor chip 32. Each diode 34 generates electrical signal representing the pressure variation, the electrical signal being utilized as pulse wave signal SM. In the instant embodiment, the pressure-sensitive diodes 34 serve as the pressure-sensitive semiconductor elements for the blood pressure measuring apparatus. Further, the externally threaded member 20, nut member 22, motor 24 and other members cooperate with each other to function as the pressing means for pressing the diodes 34 against the body surface 18. The presser plate 30 is secured to the cylindrical pressure member 26 via an electrically insulating supporting member (not shown), so that electric leakage from the pressure plate 30 (chip 32) is prevented.

Figure 3:
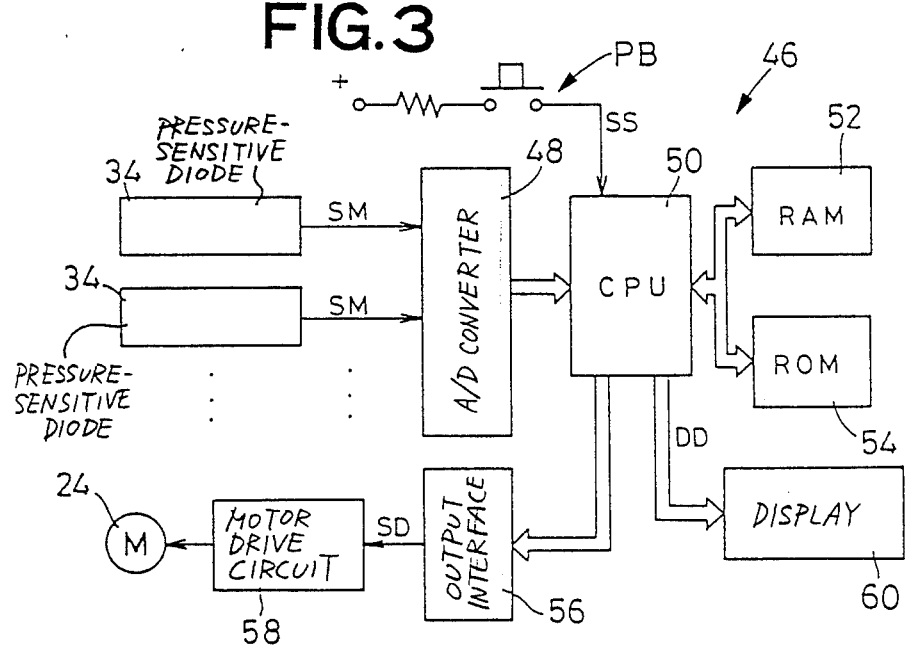
FIG. 3 is a diagrammatic view of a control device of the apparatus of FIG. 1.

In the upper room 10a of the housing 10, is disposed a control device 46 for processing the pulse wave signals SM from the pressure-sensitive diodes 34. The control device 46 includes an electrical circuit shown in FIG. 3. Each pulse wave signal SM is transmitted to an amplifier (not shown), and a band-pass filter (not shown) which transmits only the frequency component corresponding to the pulse wave signal SM. Subsequently the pulse wave signal SM is supplied to an A/D converter 48, which converts the signal SM into digital signal and applies the signal to a CPU (central processing unit) 50. The CPU 50 also receives activation signal SS from a button switch PB which is manually operable from outside the housing 10 for activating the motor 24 to effect the pressing of the presser plate 30 (diodes 34) against the body surface 18.

The CPU 50 is coupled to a RAM (random access memory) 52 and a ROM (read only memory) 54, via data bus, and cooperates therewith to form a microcomputer. The CPU 50 processes the received signals according to programs pre-stored in the ROM 54 by utilizing the temporary-storage function of the RAM 52, and generates drive signal SD to a motor drive circuit 58 via an output interface 56. The motor drive circuit 58 adjusts operation amount of the motor 24 based on the received signal SD. Concurrently, the CPU 50 supplies display signal DD representing the maximum and minimum blood pressure determined based on the pulse wave signals SM, to a display 60, which displays numeral characters or bar graphs representing the blood pressure according to the received signal DD. The display 60 is disposed and supported at an upper opening 11 of the housing 10, and accordingly the displayed blood pressure is externally observable by the subject or medical staff.

Figure 4:
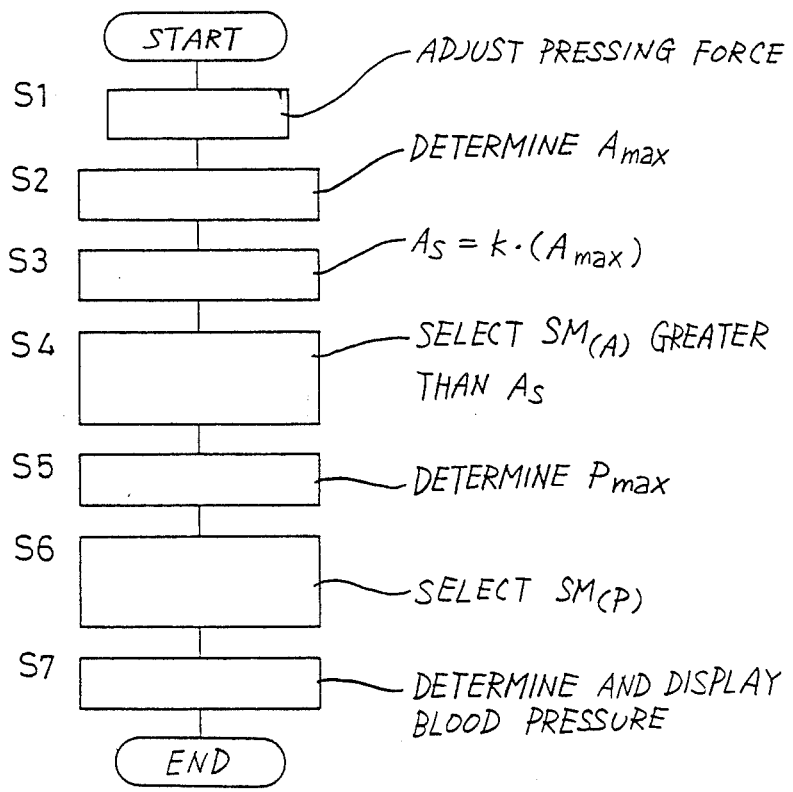
FIG. 4 is a flow chart partially illustrating the operation of the apparatus of FIG. 1.

Referring to FIG. 4, there is illustrated the flow chart for the signal processing routine executed by the control device 46. There will be described the operation of the instant blood pressure measuring apparatus, in conjunction with the flow chart.

Initially, upon operation of the button switch PB with the housing 10 set on the wrist 14 with the band 12 such that the presser plate 30 covers the body surface 18 right above the radial artery 40, the CPU 50 executes step S1 at which the CPU 50 controls the motor drive circuit 58 to press the presser plate 30 (presser member 26) against the body surface 18 with an optimum pressing force. More specifically described, the CPU 50 controls operation amount of the motor 24 by generating the drive signal SD to the motor drive circuit 58, so as to move the presser plate 30 to an optimum vertical position (as viewed in FIG. 1). The optimum pressing force or optimum vertical position is determined by the CPU 50 based on amplitude or magnitude of the pulse wave signal SM, for example, when the amplitudes of pulse wave signals SM from diodes 34 which are positioned on the body surface right above the artery 40 have become substantially equal to each other, or when the magnitude of a pulse wave signal SM from a diode 34 which is positioned at the middle of the body surface right above the artery 40 has become lower than those from the other diodes 34 located on both sides of the middle diode 34.

Figure 5:
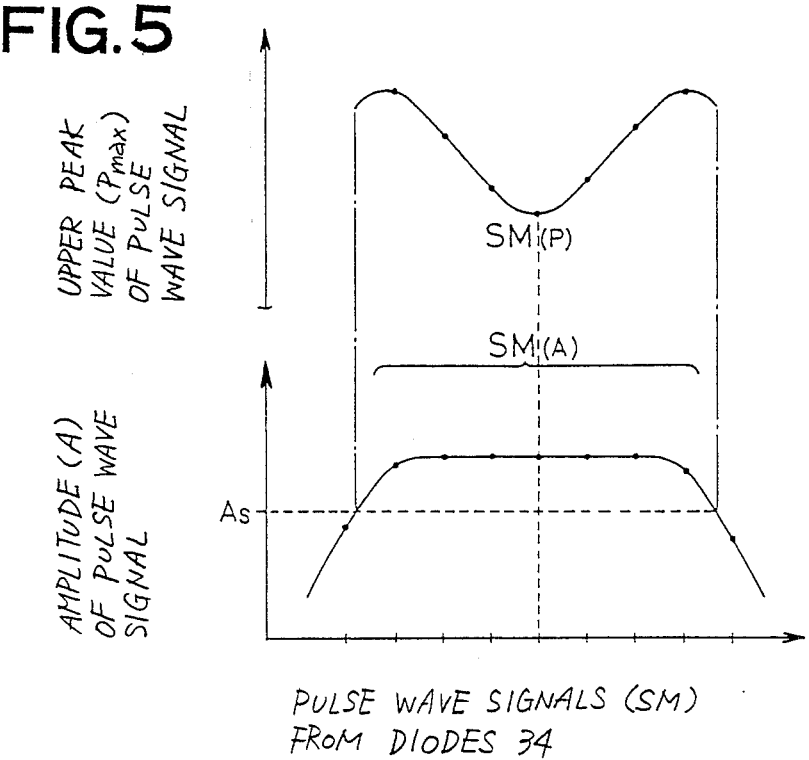
FIG. 5 is a graph illustrating varying trends in amplitude and upper peak value of pulse wave signals from a plurality of pressure-sensitive diodes of the pressure sensor of FIG. 2 which diodes are arranged along a line perpendicular to an arterial vessel from which blood pressure is detected.

Step S1 is followed by step S2 at which the CPU 50 determines the amplitudes A of the pulse wave signals SM from the multiplicity of pressure-sensitive diodes 34 arranged along a straight line substantially perpendicular to the radial artery 40, and selects a maximum amplitude $A_{max}$. Subsequently, at step S3 a reference value $A_S$ is calculated by multiplying the maximum amplitude $A_{max}$ by a predetermined coefficient k (1 > k > 0). Step S3 is followed by step S4 at which, as shown in the lower portion of the graph of FIG. 5, a group of pulse wave signals $SM_{(A)}$ whose amplitudes are greater than the reference value $A_S$, are selected. The selected signals $SM_{(A)}$ are the signals SM supplied from a group of pressure-sensitive diodes 34 positioned right above the artery 40. In other words, the amplitudes A of the group of diodes 34 right above the artery 40 are greater than those of the other diodes 34 on both sides of the group of diodes 34. In the present embodiment, the selected signals $SM_{(A)}$ includes at least three signals SM from at least three diodes 34 right above the artery 40. Since the reference value $A_S$ is determined based on the maximum amplitude $A_{max}$, the selection of the group of the pulse wave signals $SM_{(A)}$ right above the artery 40 is effected with accuracy, for example without influence from physical or physilological differences among subjects.

Step S4 is followed by step S5 at which the CPU 50 determines an upper peak value (maximum value) $P_{max}$ of each of the pulse wave signals $SM_{(A)}$ selected at step S4. The upper peak value $P_{max}$ corresponds to systolic blood pressure in the artery 40. At the following step S6, a pulse wave signal $SM_{(A)}$ whose upper peak value $P_{max}$ is smaller than those of the other signals $SM_{(A)}$ is selected as signal $SM_{(P)}$. As shown in the upper portion of the graph of FIG. 5, the selected signal $SM_{(P)}$ is the signal $SM_{(A)}$ from a diode 34 which is positioned at the middle of the body surface right above the artery 40. In other words, the upper peak value $P_{max}$ of the pulse wave signal SM from the diode 34 located at the middle of the body surface right above the artery 40, is smaller than those from the other diodes 34 on both sides of the middle diode 34. Stated further differently, the selected signal $SM_{(P)}$ is the signal $SM_{(A)}$ whose upper peak value $P_{max}$ corresponds to a minimal value of the upper curve of the graph of FIG. 5 which represents a distribution of upper peak values $P_{max}$ of the signals $SM_{(A)}$ taken in the direction perpendicular to the artery 40.

Once the pulse wave signal $SM_{(P)}$ is selected, the CPU 50 continuously reads in the signal $SM_{(P)}$ supplied from the corresponding diode 34, and at step S7 the CPU 50 determines the maximum and minimum blood pressure based on the signal $SM_{(P)}$ and generates display signal DD representing the determined blood pressure. Thus, the display 60 continuously displays the blood pressure. The reason for determining blood pressure based on the signal $SM_{(P)}$ from the diode 34 located at the middle of the body surface right above the artery 40, is that the signal $SM_{(P)}$ is free from influence from tension of the wall of the artery 40 and accordingly the signal $SM_{(P)}$ accurately reflects actual pressure oscillation (pulse wave) transmitted through the artery 40. Stated differently, regarding absolute value of blood pressure, the value determined based on the signal $SM_{(P)}$ is very approximate to that of the actual blood pressure in the artery 40. Thus, the upper and lower peak values $P_{max}$ and $P_{min}$ of the pulse wave signal $SM_{(P)}$ accurately corresponds to the actual maximum and minimum blood pressure. Once the positional relationship of the presser plate 30 relative to the artery 40 is changed due to physical motion of the subject, for example, the previously selected pulse wave signal $SM_{(P)}$ does not accurately represent the actual blood pressure It is therefore preferred that steps S2-S6 be repeated to update the signal $SM_{(P)}$ by selecting different signals SM (or different diodes 34) at suitable time intervals or each time a predetermined number of pulses have been detected. In that case, the apparatus is capable of continuously measuring accurate blood pressure, even in the case where the positional relationship between the pressure plate 30 (diodes 34) and the body surface 18 (artery 40) is changed.

All the elements or parts for the instant blood pressure measuring apparatus are accommodated in the housing 10. Specifically described, the presser plate 30 including the multiplicity of pressure-sensitive diodes 34, is disposed in the lower room 10b of the housing 10. Furthermore, the housing 10 accommodates the pressing means for pressing the presser plate 30 against the body surface 18, namely the motor 24, the nut member 22 and other members; the control device 46 for determining blood pressure based on the pulse wave signal SM; and the display 60 for displaying the blood pressure determined by the control device 46. Accordingly, blood pressure measurement is effected by simply setting the apparatus (housing 10) on the wrist 14 with the band 12 and operating the button switch PB. Further, the apparatus permits easier handling and conveyance than the prior device having air piping and/or electrical wiring for connecting between a housing thereof set on a body surface and external elements thereof. Moreover, the apparatus by no means restricts activity of the subject, in contrast to the above-indicated prior device.

While the present invention has been described in its preferred embodiment with detailed particularities, it is to be understood that the invention may be embodied with various modifications.

For example, although in the illustrated embodiment the display 60 is provided on the housing 10, it is possible to employ memory or the like for storing blood pressure measurements, in place of or in addition to the display 60. Further, it is possible to concurrently monitor blood pressure regarding a plurality of subjects in a room remote from the subjects, by using a radio telemeter in each blood pressure apparatus (housing 10).

While in the illustrated embodiment the pressing means is constituted by the motor 24, nut member 22 and other members, the combination of a diaphragm and an air pump, may serve as the pressing means.

Furthermore, it is possible to employ well-known sensors such as semiconductor strain gauges or pressure-sensitive transistors as the pressure sensor, in place of the pressure-sensitive diodes 34 used in the illustrated embodiment.

While in the illustrated embodiment the control device 46 selects one pulse wave signal $SM_{(P)}$ from the pulse wave signals SM generated by the multiplicity of pressure-sensitive diodes 34 and determines blood pressure based on the selected signal $SM_{(P)}$, according to the flow chart of FIG. 4 for the signal processing routine, it is possible to change the number of the diodes 34 and/or the arrangement of the flow chart for the signal processing routine so long as blood pressure in the artery 40 is determined through detection of the pulse wave produced from the artery 40.

Although in the illustrated embodiment both maximum and minimum blood pressure is measured, it is possible to adapt the apparatus to measure only one of the maximum and minimum blood pressure or average value of the maximum and minimum blood pressure.

While in the illustrated embodiment the microcomputer or software is adapted to select the pulse wave signal $SM_{(P)}$ for blood pressure measurement, it is possible to provide a logic circuit or hardware for effecting the same operation, namely, selection of the signal $SM_{(P)}$.

Furthermore, while the illustrated apparatus is adapted to detect pulse wave from a radial artery (40) to measure blood pressure, the principle of the present invention is applicable to apparatus of other types adapted to detect pulse wave from a carotid artery or a vein for the same purpose. It is possible to measure blood pressure in a vein although it does not produce pulse wave or transmit pressure oscillation.

It is to be understood that the present invention may be embodied with other modifications, changes and improvements which may occur to those skilled in the art without departing from the spirit and scope of the invention as defined in the appended claims.

What is claimed is:

1. A blood pressure measuring apparatus comprising:
    a housing detachably set on a body surface of a subject;
    a cylindrical member accommodated in said housing;
    a pressure sensor secured to one of axial ends of said cylindrical member, said pressure sensor being opposed to said body surface when said housing is set on said body surface, said pressure sensor being pressed against said body surface so as to detect pulse wave produced from an arterial vessel of said subject, said pressure sensor generating a pulse wave signal representing the detected pulse wave;
    pressing means for pressing said pressure sensor against said body surface by moving said cylindrical member toward said body surface, said pressing means comprising (a) an externally threaded member secured to said housing and having an axis, said axis being substantially perpendicular to said body surface when said housing is set on said body surface, (b) an internally threaded member engaged with said externally threaded member and having a multiplicity of outer teeth formed in an outer circumference thereof, (c) a motor having an output shaft, and (d) a pinion secured to said output shaft of said motor and engaged with said outer teeth of said internally threaded member, the other axial end of said cylindrical member being fitted on said externally threaded member and engaged with said internally threaded member such that said cylindrical member is coaxial with said externally and internally threaded members,
    said pressing means further comprising (e) a means for guiding said cylindrical member along said axis of said externally threaded member without causing rotation of said cylindrical member about said axis, and (f) a means for permitting said internally threaded member to be rotated relative to said cylindrical member on said externally threaded member and thereby be moved together with said cylindrical member along said axis, whereby said pressure sensor secured to said cylindrical member is moved along said axis toward or away from said body surface without rotation of said pressure sensor about said axis when said motor is operated and consequently said internally threaded member is rotated on said externally threaded member and thereby is moved along said axis;

control means for determining an optimum pressing force of said pressing means based on said pulse wave signal, and controlling said pressing means to press said pressure sensor against said body surface with said optimum pressing force, said controlling means determining a blood pressure in said arterial vessel based on the pulse wave signal supplied from said pressure sensor pressed with said optimum pressing force; and said pressing means and said control means being accommodated in said housing.

2. The apparatus as set forth in claim 1, further comprising a display device for displaying said blood pressure, said display device being provided on one of opposite outer surfaces of said housing, the other of said opposite outer surfaces being opposed to said body surface when said housing is set on said body surface.

3. The apparatus as set forth in claim 1, wherein said pressure sensor includes:
   a semiconductor chip; and
   a plurality of pressure-sensitive semiconductor elements arranged along a line on said semiconductor chip, each of said semiconductor elements generating the pulse wave signal.

4. The apparatus as set forth in claim 3, wherein said control means selects one of said plurality of pressure-sensitive semiconductor elements which is located right above said arterial vessel, said control means monitoring said blood pressure of said subject based on the pulse wave signal from the selected semiconductor element.

5. The apparatus as set forth in claim 1, wherein said control means controls the pressing force of said pressing means applied to said pressure sensor, by changing the operation amount of said motor based on said pulse wave signal from said pressure sensor.

* * * * *